1

(12) United States Patent
Sen (10) Patent No.: US 10,016,458 B2
(45) Date of Patent: Jul. 10, 2018

(54) P53 SILENCED ENDOTHELIAL PROGENITOR CELLS FOR DIABETES

(71) Applicant: Baystate Health, Inc., Springfield, MA (US)

(72) Inventor: Sabyasachi Sen, Longmeadow, MA (US)

(73) Assignee: Baystate Health, Inc., Springfield, MA (US)

( * ) Notice: Subject to any disclaimer, the term of this patent is extended or adjusted under 35 U.S.C. 154(b) by 0 days.

(21) Appl. No.: 13/794,567

(22) Filed: Mar. 11, 2013

(65) Prior Publication Data

US 2013/0273014 A1   Oct. 17, 2013

Related U.S. Application Data

(60) Provisional application No. 61/624,906, filed on Apr. 16, 2012.

(51) Int. Cl.
 *A61K 35/14*    (2015.01)
 *A61K 35/44*    (2015.01)

(52) U.S. Cl.
 CPC .............. *A61K 35/14* (2013.01); *A61K 35/44* (2013.01)

(58) Field of Classification Search
 CPC ................................ A61K 35/44; A61K 35/14
 USPC ......................................................... 424/93.2
 See application file for complete search history.

(56) References Cited

U.S. PATENT DOCUMENTS

| | | | |
|---|---|---|---|
| 2003/0232050 A1* | 12/2003 | Isner et al. | ................ 424/144.1 |
| 2009/0305987 A1 | 12/2009 | Thayer et al. | |
| 2011/0160121 A1 | 6/2011 | Brizzi et al. | |

FOREIGN PATENT DOCUMENTS

| | | |
|---|---|---|
| EP | 2194121 A1 | 6/2010 |
| WO | WO 2008/156728 A1 | 12/2008 |
| WO | WO 2010/115052 A2 | 10/2010 |

OTHER PUBLICATIONS

Nguyen et al 2010, Wound Repair Regen. 18:553-559.*
Rosso et al 2006, JBC 281:4339-4347.*
Jazayeri et al 2008, Plast. Reconstr. Surg. 121:1135-1143.*
Bernardi et al 2012 & Jun. 2011, Exp. Diabetes. Res. 2012:1-10.*
Jarajapu et al 2010, Circ Res. 106 (5): pp. 1-31.*
Choi et al 2004, JBC 279:49430-49438.*
[No Author Listed] Centers for Disease Control and Prevention. National diabetes fact sheet: national estimates and general information on diabetes and prediabetes in the United States, 2011. Atlanta, GA. U.S. Department of Health and Human Services, Centers for Disease Control and Prevention. 12 pages.

[No Author Listed] Standards of Medical Care in Diabetes—2011, Diabetes Care; Jan. 2011, vol. 34, Supplement 1: S11-S61.
Asahara et al., Isolation of putative progenitor endothelial cells for angiogenesis. Science. Feb. 14, 1997;275(5302):964-7.
Bernardi et al., Cell-Based Therapies for Diabetic Complications. Experimental Diab Res. 2012;2012:1-10. doi:10.1155/2012/872504.
Compton et al., Mitochondrial Dysfunction Impairs Tumor Suppressor p53 Expression/Function. J Biol Chem. Jun. 10, 2011; 286(23):20297-312. doi: 10.1074/jbc.M110.163063. Epub Apr. 18, 2011.
Fadini et al., Significance of Endothelial Progenitor Cells in Subjects With Diabetes. Diabetes Care. May 2007;30(5):1305-13.
Fadini et al., Time course and mechanisms of circulating progenitor cell reduction in the natural history of type 2 diabetes. Diabetes Care. May 2010;33(5):1097-102. doi: 10.2337/dc09-1999. Epub Feb. 11, 2010.
He et al., Knockdown of p53 by RNAi in ES cells facilitates RA-induced differentiation into muscle cells. Biochem Biophys Res Commun. Sep. 30, 2005;335(3):676-83.
Heidersbach et al., RNA interference in embryonic stem cells and the prospects for future therapies. Gene Ther. 2006;13:478-86.
Hori et al., Growth inhibitors promote differentiation of insulin-producing tissue from embryonic stem cells. Proc Natl Acad Sci. Dec. 10, 2002;99(25):16105-10.
Jarajapu et al., The promise of cell-based therapies for diabetic complications: challenges and solutions. Circ Res. Mar. 19, 2010;106(5):854-69. doi: 10.1161/CIRCRESAHA.109.213140. Review. Erratum in: Circ Res. Apr. 30, 2010;106(8):e7.
Kalka et al., Transplantation of ex vivo expanded endothelial progenitor cells for therapeutic neovascularization. Proc Natl Acad Sci U S A. Mar. 28, 2000; 97(7): 3422-3427. Published online Mar. 21, 2000.
Kappel et al., Silencing of mammalian genes by tetracycline-inducible shRNA expression. Nat Protoc. 2007;2(12):3257-69.
Kawamoto et al., Intramyocardial transplantation of autologous endothelial progenitor cells for therapeutic neovascularization of myocardial ischemia. Circulation. Jan. 28, 2003;107(3):461-8.
Losordo et al., ACT34-CMI Investigators. Intramyocardial, autologous CD34+ cell therapy for refractory angina. Circ Res. Aug. 5, 2011;109(4):428-36. doi: 10.1161/CIRCRESAHA.111.245993. Epub Jul. 7, 2011.
Losordo et al., Intramyocardial transplantation of autologous CD34+ stem cells for intractable angina: a phase I/IIa double-blind, randomized controlled trial. Circulation. Jun. 2007;115(25):3165-72. Epub Jun. 11, 2007.
Miyauchi et al., Akt negatively regulates the in vitro lifespan of human endothelial cells via a p53/p21-dependent pathway. EMBO J. 2004; 23(1):212-20.
Morales et al., Estrogen promotes angiogenic activity in human umbilical vein endothelial cells in vitro and in a murine model. Circulation. Feb. 1, 1995;91(3):755-63.
Mund et al., Endothelial progenitor cells and cardiovascular cell-based therapies. Cytotherapy. 2009;11(2):103-13. doi: 10.1080/14653240802714827.
Nishiyama et al., Functional analysis of an established mouse vascular endothelial cell line. J Vasc Res. 2007;44(2):138-48. Epub Jan. 11, 2007.

(Continued)

*Primary Examiner* — Christopher M Babic
*Assistant Examiner* — Kelaginamane Hiriyanna
(74) *Attorney, Agent, or Firm* — Wolf, Greenfield & Sacks, P.C.

(57) ABSTRACT

The invention provides, inter alia, methods for treating vascular deficiencies, including those in diabetic subjects, by transplanting endothelial progenitor cells with transiently reduced p53 expression.

16 Claims, 5 Drawing Sheets

(56) References Cited

OTHER PUBLICATIONS

Petrelli et al., Strategies to Reverse Endothelial Progenitor Cell Dysfunction in Diabetes. Experimental Diabetes Research. 2012;2012:1-9.

Rosso et al., p53 Mediates the accelerated onset of senescence of endothelial progenitor cells in diabetes. J Biol Chem. Feb. 17, 2006;281(7):4339-47. Epub Dec. 9, 2005.

Rubinson et al., A lentivirus-based system to functionally silence genes in primary mammalian cells, stem cells and transgenic mice by RNA interference. Nat Genet. Mar. 2003;33(3):401-6, Epub Feb. 18, 2003. Erratum in Nat Genet Jun. 2007;39(6):803. Zhang, Mingdi [added]. Nat Genet. Jun. 2003;34(2):231.

Sen et al., Autologous transplantation of endothelial progenitor cells genetically modified by adeno-associated viral vector delivering insulin-like growth factor-1 gene after myocardial infarction. Hum Gene Ther. Oct. 2010;21(10):1327-34. doi: 10.1089/hum.2010.006.

Sen et al., Gene delivery to the vasculature mediated by low-titre adeno-associated virus serotypes 1 and 5. J Gene Med. Feb. 2008;10(2):143-51.

Sen et al., P53 silenced endothelial progenitor stem cells (EPC) improve collateral circulation post femoral artery occlusion in diabetic mice. American Heart Association Arteriosclerosis, Thrombosis and Vascular Biology Scientific Sessions. Chicago, IL. Apr. 18-Apr. 20, 2012. Abstract 117. 1 page.

Sen et al., Regenerative Potential of P53 Silenced Human Endothelial Progenitor Stem Cells (hEPCs) In Diabetes. Circ. 2010;122:A12118.

Shen et al., Gene silencing by adenovirus-delivered siRNA. FEBS Letters. Mar. 27, 2003; 539:111-4.

Soria et al., Insulin-secreting cells derived from embryonic stem cells normalize glycemia in streptozotocin-induced diabetic mice. Diabetes. Feb. 2000;49(2):1-6.

Spinetti et al., Diabetes and vessel wall remodelling: from mechanistic insights to regenerative therapies. Cardiovasc Res. May 1, 2008;78(2):265-73. doi: 10.1093/cvr/cvn039. Epub Feb. 15, 2008.

Utikal et al., Immortalization eliminates a roadblock during cellular reprogramming into iPS cells. Nature. Aug. 27, 2009;460(7259):1145-8. doi: 10.1038/nature08285. Epub Aug. 9, 2009.

Ventura et al., Cre-lox-regulated conditional RNA interference from transgenes. Proc. Natl. Acad. Sci. Jul. 13, 2004;101(28):10380-5.

Brummelkamp et al., A System for Stable Expression of Short Intefering RNAs in Mammalian Cells. Science. Apr. 19, 2002; 296:550-553.

Daneman, Type 1 diabetes. Lancet. Mar. 11, 2006;367(9513):847-58.

Kalka et al., Transplantation of ex vivo expanded endothelial progenitor cells for therapeutic neovascularization. Proc Natl Acad Sci U S A. Mar. 28, 2000;97(7):3422-7.

* cited by examiner

P53 SILENCED ENDOTHELIAL PROGENITOR CELLS FOR DIABETES

RELATED APPLICATIONS

This application claims priority under 35 U.S.C. § 119(e) to U.S. Provisional Application Ser. No. 61/624,906, entitled "p53 SILENCED ENDOTHELIAL PROGENITOR CELLS (EPC) FOR DIABETES" filed on Apr. 16, 2012, which is incorporated by reference herein in its entirety.

FIELD OF INVENTION

The invention relates to the use of genetically modified endothelial progenitor cells (EPC) for the amelioration of vascular symptoms and outcomes associated with diabetes.

BACKGROUND OF INVENTION

Diabetes is a disease which has reached epic proportions in the US. Nine percent of the adult population has been diagnosed as diabetic and more than 30% of adults are considered pre-diabetic[1], costing Americans an astounding $174B/yr. Patients with diabetes often present with concomitant illnesses and are prone to serious vaso-occlusive complications.

Every day, 230 patients undergo diabetes-related amputation[1] due to peripheral vascular disease. Peripheral vascular disease in these patients most often occurs secondary to near-total or total occlusion of major vessels in the limb such as the femoral or tibial artery.

SUMMARY OF INVENTION

The invention relates broadly to the use of genetically modified endothelial progenitor cells (EPC) to treat vascular conditions associated with diabetes. More specifically, the invention contemplates modifying such EPC in order to transiently and temporally reduce (and preferably silence) p53 expression in EPCs. This transient, temporal silencing occurs during the differentiation of EPCs into mature endothelial cells. The invention is premised in part on the discovery that EPC but not their more differentiated and mature progeny are susceptible to the effects of high glucose.

The invention therefore provides methods for reducing expression of p53 in EPCs during EPC differentiation. In some embodiments, p53 expression is reduced completely (i.e., silenced). In some embodiments, it is reduced by to 75%, 50%, 25%, 10%, or to 5% of the pre-treatment levels in the EPC. The p53 expression may be reduced through the use of p53 specific siRNA or shRNA. Alternatively, p53 expression may be reduced through the use of regulatory elements that are temporally controlled through external agents. As used herein, p53 expression may be measured in terms of p53 mRNA expression or p53 protein expression.

In one aspect, the invention provides a method comprising administering to a subject having diabetes a genetically modified EPC, wherein the genetically modified EPC is characterized by reduced p53 expression. Such EPC may be referred to herein as genetically modified EPC or p53⁻, or p53-silenced EPC. Reduced p53 expression refers to p53 expression in the modified EPC that is reduced relative to an unmodified EPC, including p53 expression in the same EPC prior to genetic modification. In some embodiments, reduced p53 expression is no p53 expression.

The genetically modified EPC may comprise p53 specific siRNA or p53-specific shRNA. The siRNA or shRNA may be provided by an adenoviral vector. Adenoviral vectors have been demonstrated, in accordance with the invention, to express transcripts for a length of time that approximates the time it takes an EPC to differentiate into its mature endothelial cell. Thus, the adenovirus is functional during the time the EPC is differentiating to mature endothelium, thereby reducing (or eliminating) p53 from the cell. This renders the cell less likely to undergo apoptosis (programmed cell death) in response to diabetic environmental conditions such as high glucose. The transient down-regulation lasts for about 2-4 weeks, in some embodiments.

In some embodiments, the genetically modified EPC are autologous EPC (i.e., they are obtained from the subject being treated). In some embodiments, the genetically modified EPC may be obtained from a sibling, parent or child of the subject being treated. In some embodiments, the genetically modified EPC are obtained from an individual that is not genetically related to the subject being treated. In most embodiments, the subject being treated is a human subject.

The subject having diabetes may receive genetically modified EPC once or several times. For example, the genetically modified EPC may be administered at one month intervals (i.e., every month), two month intervals, three month intervals, four month intervals, five month intervals, or six month intervals, or at greater intervals of time.

The genetically modified EPC may be administered locally to the subject, including to a limb (leg or arm) or other body region that is experiencing vascular effects of diabetes. As used herein, local administration excludes topical administration such as to the skin.

In another aspect, the invention provides a method comprising reducing p53 expression in an EPC harvested from a donor, thereby forming p53 silenced EPC, and administering the p53 silenced EPC to a subject having diabetes. The subject may have vaso-occlusive complications of diabetes. The donor may be the subject being treated, or it may be a relative of the subject being treated, or it may be unrelated to the subject being treated. The EPC may be harvested from a population of mononuclear cells of peripheral blood or may be bone marrow derived. They are usually cell surface marker, CD34+ cells.

The methods of the invention are useful in treating ischemia and its effects in diabetic subjects by reducing peripheral vascular disease in such subjects or reducing the effects of peripheral vascular disease in such subjects.

BRIEF DESCRIPTION OF FIGURES

FIG. 5 Inhibition of p53 expression by Lenti shRNA in Human Umbilical Vein Endothelial Cells (HUVEC). A. Expression of p53 and p21, a target gene of p53, is inhibited for at least 28 days in culture. However, the expression levels of EC markers in HUVEC cells were not altered by p53 inhibition. HUVEC cells are infected with lentiviruses carrying either eGFPshRNA or p53shRNA. Total RNAs were collected after 4 weeks post infection before subjecting to QRT-PCR analysis. Bar values are the average from duplicates. B. Silencing p53 in HUVEC cells resulted in increased cell survival in normal (NG) and high glucose (HG) medium compared to GFP control. p53-silenced (p53shRNA) or control (GFPshRNA) HUVEC cells were seeded onto 6-well plates (50,000/well) with or without 20 mM glucose supplemented in medium. Total viable cells were counted. Dot values represent the average of cells from triplicate wells at each time point.

FIGS. 7 and 8 indicate that there is more capillary or collateral formation (indicated by thin arrows) when p53 silenced EPCs are delivered IM around the occlusion compared to normal wild type EPC or saline.

DETAILED DESCRIPTION OF INVENTION

The invention provides a method for harnessing the regenerative capacity of endothelial progenitor cells to treat ischemic diabetic complications by circumventing vascular blockage and augmenting collateral circulation. The degree of collateral vessel formation is important for salvaging an ischemic leg[2,3]. Endothelial progenitor stem cells (EPCs) which are better defined as CD34+ cells are short-term stem cells poised to form capillary-like structures that repair damaged blood vessels. EPCs have been shown to improve healing in hind limb ischemia and myocardial infarction by promoting and participating in angiogenesis[2-4].

EPCs are a subset of the total mononuclear cell population (tMNCs) that possess an enhanced potential for differentiation towards the endothelial-cell lineage. Typically, EPCs are selected from tMNCs via the expression of both hematopoietic stem-cell markers and endothelial-cell markers, such as CD34, or by culturing tMNCs in media selective for endothelial cells. Both EPCs and tMNCs participate in vascular growth and regeneration, and their potential use for treatment of myocardial injury or disease has been evaluated in early-phase clinical studies. Direct comparisons between EPCs and tMNCs are rare, but the available evidence appears to favor EPCs, particularly CD34+ cells, and the potency of EPCs may be increased as much as 30-fold through genetic modification[5-8].

The invention is based, at least in part, upon the demonstrate that significant numbers of CD34+ endothelial progenitor cells are non-functional or dead within 48 hrs (2 days) of exposure to high glucose, and that this is associated with activation of the pro-apoptotic p53 gene and its downstream apoptotic pathway. We have also demonstrated that human umbilical cord vein endothelial cells (HUVEC), unlike human EPC (hEPC), are much less susceptible to hyperglycemic cell death even up to 10 days of high glucose (HG) exposure, though proliferation may be affected.

The invention therefore contemplates that inhibition of p53 provides a means to improve survival of CD34+ cells in hyperglycemic conditions until they differentiate into mature endothelium, at which stage the mature cells are not as susceptible to apoptotic injury. The invention contemplates transient p53 silencing for 2-4 weeks, thereby allowing progenitor CD34+ cells to become mature endothelial cells. In some embodiments, this can be achieved using third generation adenoviral vectors which are less immunogenic. Accordingly, the invention contemplates a therapeutic benefit of apoptosis resistant EPC local delivery to improve collateral circulation in a setting of peripheral vascular disease and diabetes. It is intended that such therapeutic benefit may reduce the likelihood of amputation of limbs (such as the lower limb, which is often impacted by diabetes), or may at least limit the degree of amputation to below-knee amputation.

Diabetes or hyperglycemia can be characterized by the presence of reactive oxygen species (ROS), and increased presence of pro-inflammatory molecules, such as IL-6 and tumor necrosis factor-alpha. The pro-inflammatory agents in diabetes or hyperglycemia damage the vascular endothelium and reduce the number of EPCs[9] leading to the impairment of the blood-vessel repair that is essential for tissue growth and regeneration. Thus, peripheral vascular diseases and poor wound healing are common complications among patients with diabetes[10].

Careful manipulation and silencing of p53-dependent pathways in transplanted CD34+ cells may prevent vaso-occlusive disease in diabetic patients[12-14]. The invention is distinguished from other approaches aimed at p53 in that is provides a transient reduction in expression rather than a global or permanent partial or complete reduction. As is known in the art, p53 is a pro-apoptotic mediator that has been thought to possess tumor suppression activity. Its mutation to either a null or a dominant negative genotype may result in unwanted cellular proliferation. Similarly, a permanent reduction in the level of the protein may cause unwanted effects such as malignant growth. Accordingly, the invention contemplates that the modulation of p53 expression occurs only transiently with the ultimate progeny of the modified EPC having wild type levels of p53. Such transient modulation of p53 expression can be achieved using adenoviral vectors as described herein or as described by Shen et al. FEBS Letters 539: 111-114 (2003).

EXAMPLES

The invention aims to prevent p53 mediated EPC death in the presence of hygerglycemia until mature endothelium or capillaries are formed. Mature endothelial cells are much less susceptible to hyperglycemic cell death compared to human EPCs. Our preliminary results demonstrate poor survival of human EPCs and also CD34+ cells in high glucose. This is a direct consequence of elevated glucose levels and not secondary to osmolality effect. Apoptotic death of EPCs in hyperglycemia is accompanied by up-regulation of p53 in-vitro. Therefore, transient knock-down of p53 in transplanted CD34+ cells can improve their survival and can be a viable therapeutic intervention in PVD in both type 1 and 2 diabetes patients. This technique will also help to reduce the number of stem cells necessary for transplantation for new vessel formation in an apoptotic environment.

This study looks at the feasibility of using apoptosis resistant human CD34+ cells in diabetic mouse models. The concept of using p53 transiently silenced CD34+ cells in PVD treatment avoids possible mutagenesis. A renewable source for robust, apoptosis-resistant primary CD34+ would be beneficial for applications in regenerative medicine, particularly vascular regeneration in the pro-senescence condition of hyperglycemia.

Figure 1:
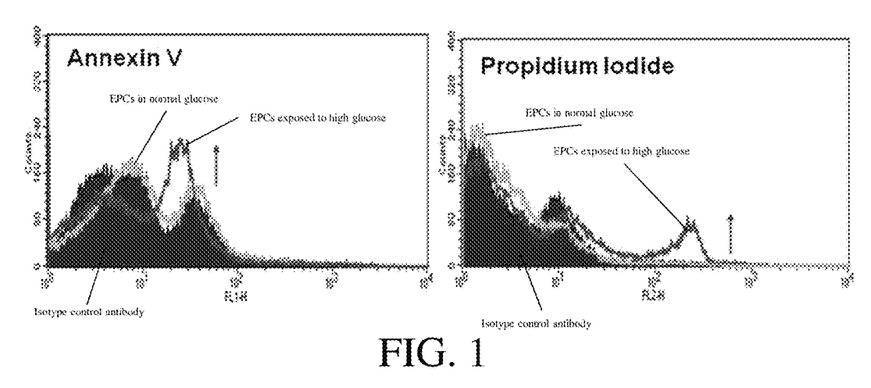
FIG. 1: Apoptotic cell death of human EPCs in hyperglycemia. FACS analysis for Annexin V (left panel) and Propidium Iodide (right panel) were used to assess cell death in EPCs. Purple color indicates isotype control antibody. Green line shows EPCs in normal glucose (5.5 mM). Pink line shows EPCs exposed to high glucose (20 mM) for 48 hrs. The arrow highlights the differences in the number of fluorescent cells between the 5.5 mM and the 20 mM glucose.

Human EPCs are sensitive to high glucose compared to mature endothelial cells. We tested survival of EPCs in high glucose solutions that mimic a diabetic setting. After 48 hours of exposure to high glucose the number of Annexin V positive cells is increased (FIG. 1, left panel) indicating initiation of apoptosis. The overall cell death was also increased as measured by permeability to propidium iodide (FIG. 1, right panel).

Figure 2:
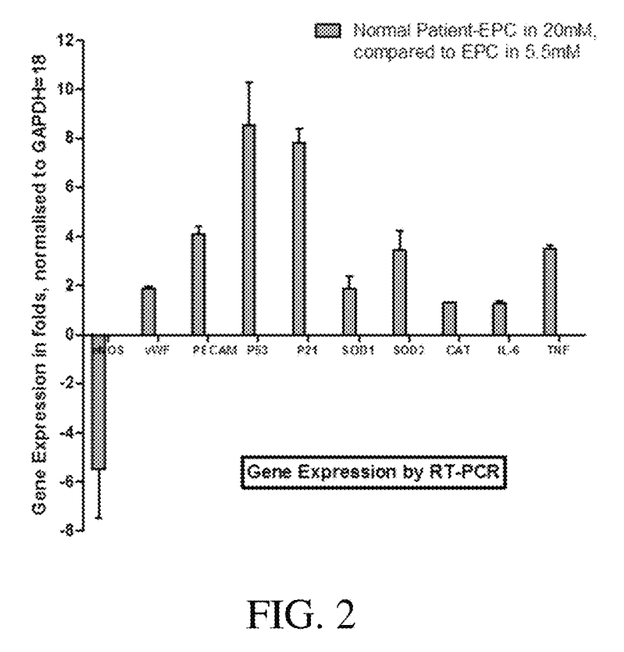
FIG. 2: Gene expression of human EPCs exposed to high glucose for 48 hrs compared to normal glucose. Expression of markers of EPCs (eNOS, vWF, PECAM), pro-apoptotic signaling (p53, p21), and endogenous anti-oxidant (SOD 1, 2 and Catalase (CAT)) and pro-inflammatory responses (IL-6, TNF) were analyzed in human EPCs. Relative expression for EPCs in high glucose (20 mM) compared to normal glucose (5.5 mM) are reported as log2 ratios converted from cycle threshold difference.

The p53 protein plays intricate roles in DNA damage repair and can promote aging by activating pathways of apoptosis and cellular senescence[12,15]. The increased death of EPCs after 48 hrs of exposure to high glucose is accompanied by activation of the p53 pathway indicated by increased levels of p53 and P21 mRNA by 7-8 fold compared to EPCs in normal levels of glucose (FIG. 2). Increases in SOD1, SOD2 and Catalase may occur in response to intra-cellular accumulation of reactive oxygen species as well as pro-inflammatory responses (IL-6, TNFα). Interestingly, hyperglycemic exposure of EPCs is accompanied by a 5-fold decrease in eNOS gene expression. SOD2, a mitochondrial antioxidant, and PECAM-1, an endothelial cell adhesion molecule, are also up-regulated by 3-4 folds.

Diminishing p53 Function Improved the Maintenance of Mouse EPC Cells

Figure 3:
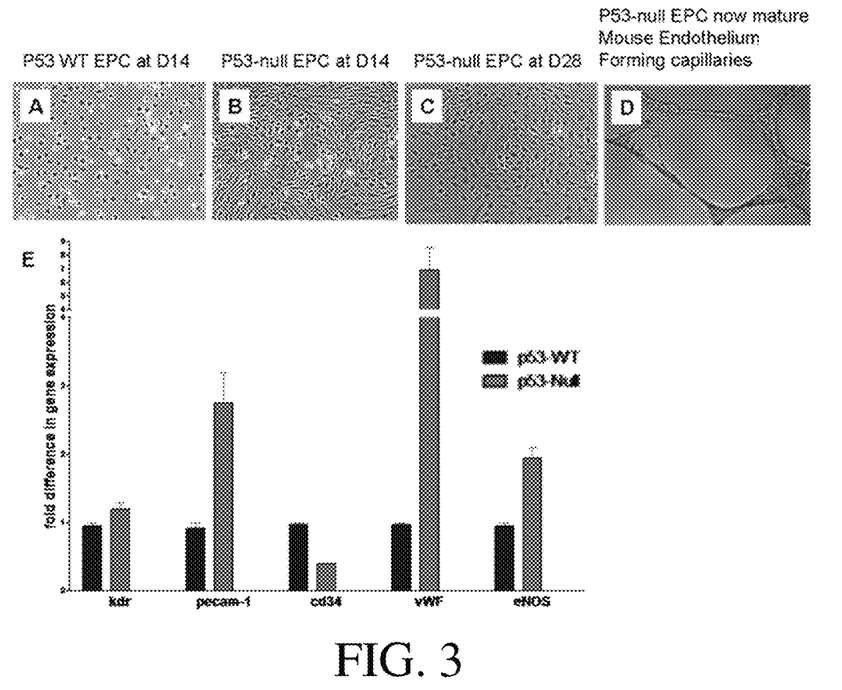
FIG. 3: Loss of p53 extends survival in vitro and differentiation of EPCs into mature endothelium. EPCs from C57BL/6 mice that were either Trp53+/+ (p53-WT) and Trp53−/− (p53-null) were maintained in culture. While the p53-WT EPCs showed poor survival at 14 days (A), the p53-null EPCs were growing (B) and were passaged through 28 days (C). The p53-null EPCs at 28 days retained capillary-forming ability when grown on Matrigel (D). Expression of markers of EPCs and mature endothelium was determined in p53-null EPCs (kdr, pecam-1, cd34, vWF, eNOS) after 14 days in culture (E).

To determine whether the death of EPCs is controlled by p53, we compared EPCs obtained from p53 wild type (p53-WT) and p53 knockout (p53-null) mice (n=6 animals for each genotype). The isolation and in vitro culture of mouse EPCs have been described previously[2-4,9,16]. Consistent with results in human EPCs, the p53-WT mouse EPCs were dying when maintained in 20 mM glucose for 14 days and cultures failed to survive at 28 days. The inability to maintain primary cultures of p53-WT mouse endothelial cells is consistent with previous reports[14,17]. In contrast, p53-null mEPCs continued to grow in culture for >28 days (FIG. 3A-C) and have yielded immortalized mEPCs. mEPCs from both C57BL/6 and BALB/c mice strains showed improved survival for p53-null EPCs.

Number of colonies formed by p53-null mEPCs were 2.2-fold higher than the number of colonies formed by p53-WT cells at day 5 of culture from 10 mls of mouse blood in each group (cell counts: 7.5 million±1.6, in p53-WT group, compared to 15.4 million±2.5, in p53-null group, P<0.05), confirming that disruption of p53 is associated with greater cell survival.

To evaluate the effect of loss of p53 on the regenerative potential, we decided to investigate whether the endothelial properties of the p53 null mEPCs are maintained in-vitro.

The p53-null EPCs readily formed capillary-like or tube-like structures when placed in Matrigel (FIG. 3D).

The state of differentiation was also evaluated using expression of specific endothelial cell (EC) markers (FIG. 3E), which showed p53 null cells were more matured.

KDR or VEGFR2 is an endothelial marker that is independent of differentiated state. Immature endothelial cell markers, CD34 and von-Willebrand's factor (vWF), were also tested along with CD31 which is primarily expressed in mature endothelial cells (EC)[5,16]. After 14 days in culture, both EC markers (CD31 and vWF) and eNOS were expressed at higher levels in p53-null EPCs compared to the p53-WT EPCs. In contrast, the immature EC marker CD34 mRNA level is low in cells obtained from p53-null compared to the p53-WT mice. KDR/VEGFR2 is expressed at similar levels in both cell lines with or without the presence of p53.

Figure 4:
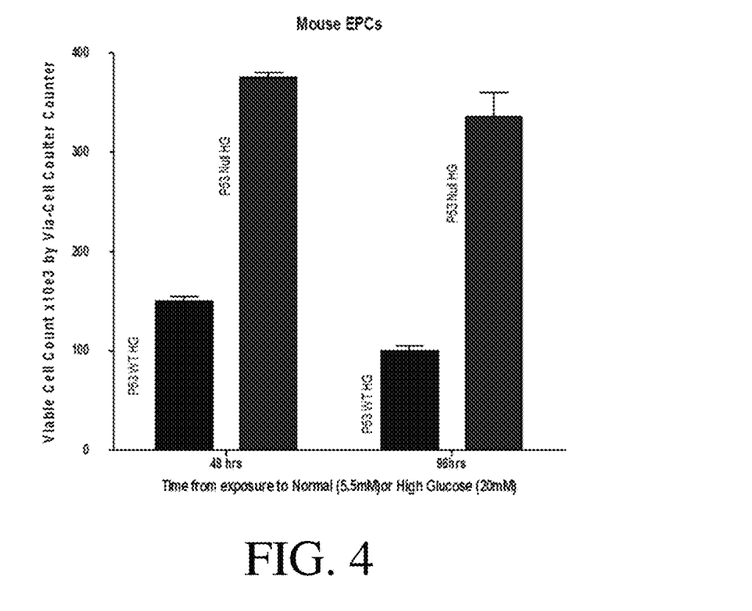
FIG. 4: p53 null EPCs (second bar) survive better than p53 WT EPCs (first bar) at 48 and 96 hrs of high glucose exposure.

Therefore, both gene expression and functional tests of tube-formation demonstrated that loss of p53 does not impair the differentiation or function of mEPCs. We have also confirmed that p53 silenced mouse EPCs indeed survive better in 20 mM glucose compared to WT-EPC in-vitro. (FIG. 4)

Inhibition of p53 Using Viral Transduction of siRNA

Figure 5:
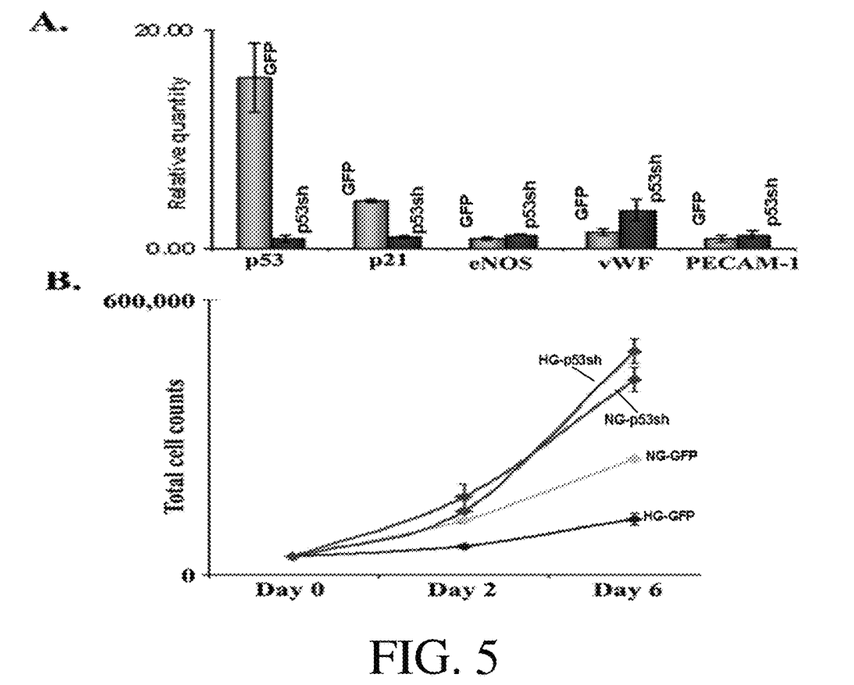

To develop EPC therapies, it will be important to be able to transduce immortalized cell line HUVEC as well as primary EPCs with siRNAs that target p53 and its downstream effectors efficiently. With HUVEC, we have used the Lentiviral vector containing encoding shRNA targeting mouse p53 (p53shRNA) or GFPshRNA as a control. Viral transduction resulted in efficient suppression of both p53 and its target genes (e.g. p21), but markers of endothelial cells (eNOS, vWF, PECAM-1) showed minimal changes (FIG. 5A). Suppression of p53 and maintenance of expression of key endothelial genes was retained for over 4 weeks in culture. We next tested whether viral-mediated knockdown of p53 rendered the HUVECs resistant to the effects of high glucose levels in the media (FIG. 5B). The HUVECs were infected then maintained in either normal glucose (NG=5.5 mM) or high glucose (HG=20 mM). The HG media reduced HUVEC proliferation at 6 days whereas the p53shRNA transduced HUVEC cells expanded.

These results indicate silencing of p53 does not disrupt mature endothelial markers for 4 weeks and efficiently protects cells from the senescence effects of hyperglycemia.

p53 Silencing in Primary Human EPCs

Figure 6:
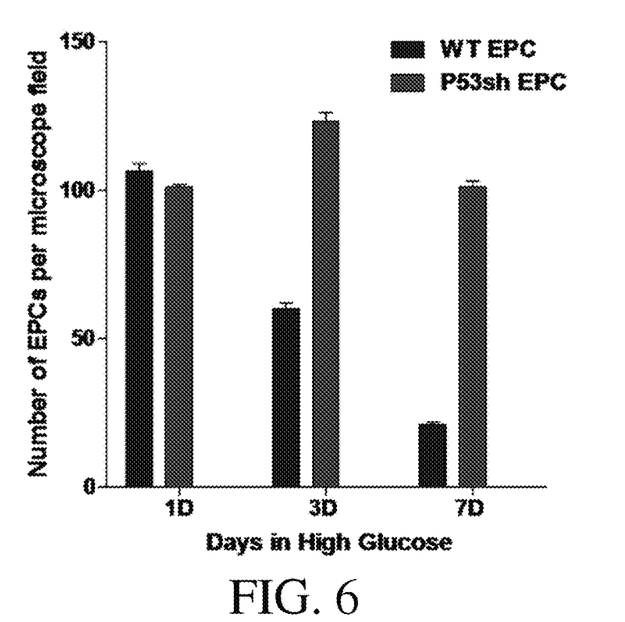
FIG. 6: Stable knockdown of p53 in primary human EPCs. Human EPCs were transduced with Lentiviruses expressing GFPshRNA or p53shRNA. We noted improved survival of p53 silenced human EPC in High Glucose by noting number of viable hEPCs (Beckman Coulter Counter) at Days 1, 3 and 7, post exposure to high glucose.

Next we used lentiviruses (Cell BioLabs) to inhibit p53 function in human EPCs in a stable manner. Primary EPCs were obtained from peripheral blood of healthy volunteers and infected with Lentivirus. Similar to mouse EPCs from p53 null animals' stable knockdown of p53 in human EPCs resulted in significantly greater survival when maintained in high glucose for 7 days (FIG. 6). This demonstrates the efficacy of p53 silencing and its downstream targets as a means to improve human EPC survival under hyperglycemic conditions.

Figure 9:
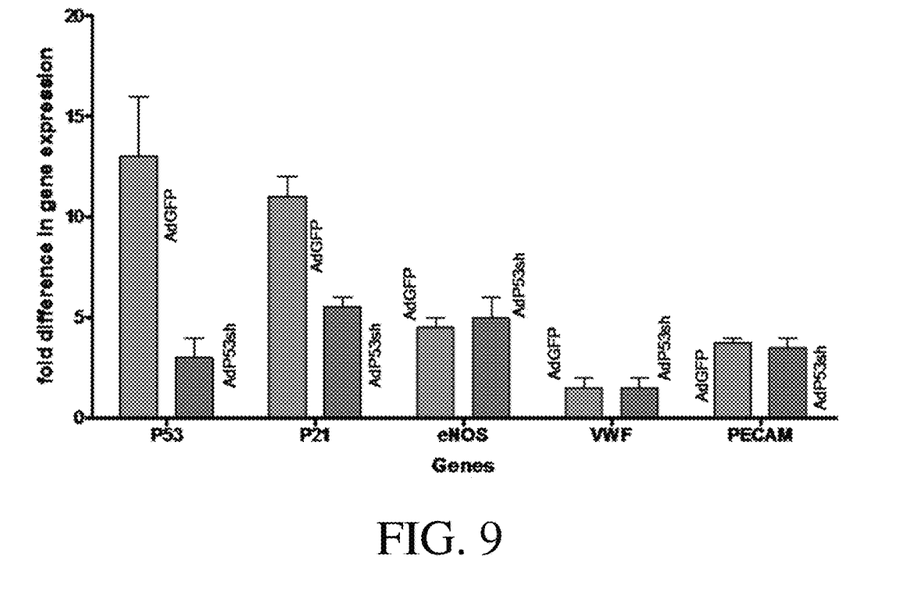
FIG. 9: Transient knockdown of p53 with adenovirus. Human EPCs were transduced with adenovirus with resultant suppression of p53 and downstream factor p21, with no loss of expression of endothelial genes of eNOS, vWF and PECAM-1.

We have also demonstrated suppression of p53 using adenovirus p53sh in human EPCs. Primary EPCs were obtained from peripheral blood of healthy volunteers and infected with adenovirus. The p53 silenced EPC using adenovirus survived in high glucose conditions while maintaining expression of key endothelial function genes tested were (by qPCR) p53, p21, eNOS, vWF and PECAM-1. (FIG. 9)

In Vivo Results

Figure 7:
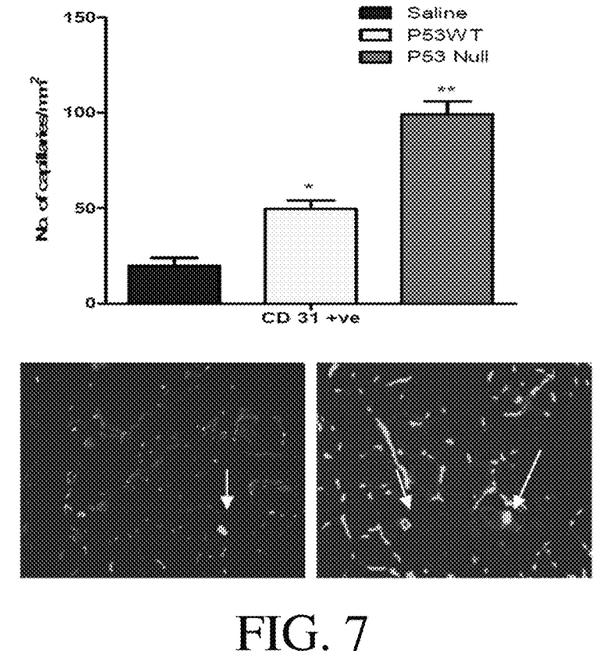
FIG. 7: Capillary density is increased in STZ induced diabetic C57B16 mouse model. Animals post femoral occlusion on right limb received saline, p53WT or p53null post right sided femoral artery occlusion. Capillary density noted on staining hind-limb musculature with Alexa-CD31 antibody. Increased CD31+ve capillary cell wall indicates increased new vessel formation. Arrows indicate capillaries that have been stained. Similar differences were noted in db/db mice also.
Figure 8:
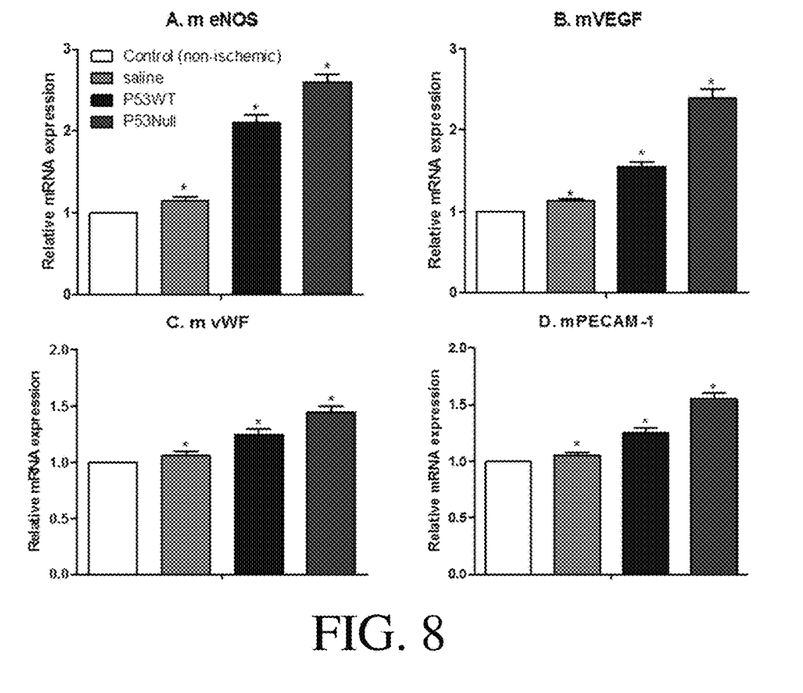
FIG. 8. Relative mRNA expression of mouse vascular genes (eNOS, VEGF, vWF and PECAM-1) in quadriceps muscle of mice: First bar represents gene expression from non-operated muscle, Second bar represents gene expression from operated muscle that received saline. Gene expression of eNOS, VEGF, vWF and PECAM-1 was highest in the operated muscles of animals that received p53 null mouse EPCs. Statistical analysis by one-way ANOVA. (*) indicate significant difference (p=0.05 level)

Our in-vivo preliminary data depicts n=6 in each group from in STZ induced WT mice (n=18) and db/db-ve mice (n=18) in FIGS. 7 and 8 respectively. Our p53 null EPC transplanted quadriceps showed more capillaries in a STZ induced diabetes mice (FIG. 7) and higher expression of vascular probes (FIG. 8) in db/db mice compared to p53 WT EPC or saline. Capillary estimation in db/db mice had similar result to STZ induced diabetic mice where both mouse types received p53 null mEPCs.

Reduced EPC counts in diabetes have been shown in trials.[5] The depletion of EPCs is, in part, due to the toxicity of high glucose levels. Increased survival of EPCs was observed in human p53-silenced EPCs under normal culture conditions and also under hyperglycemic conditions (FIG. 6). As mentioned before the cell apoptotic death secondary to p53 pathway up-regulation and may be caused by accumulation of reactive oxygen species (ROS) and/or TNFα inflammatory pathways in a state of hyperglycemia.

Method of Obtaining CD34 Positive Human Cells

Mononuclear cell population is obtained from human peripheral blood following ficoll-gradient centrifugation method. Subsequently the MNC population is passed through human CD34+ magnetic column (Miltenyi Biotech) and CD34+ population is obtained, a more homogenous population with which to work. These cells when subsequently cultured in endothelial growth media are lectin and Di acetyl LDL stain positive.

Figure 10:
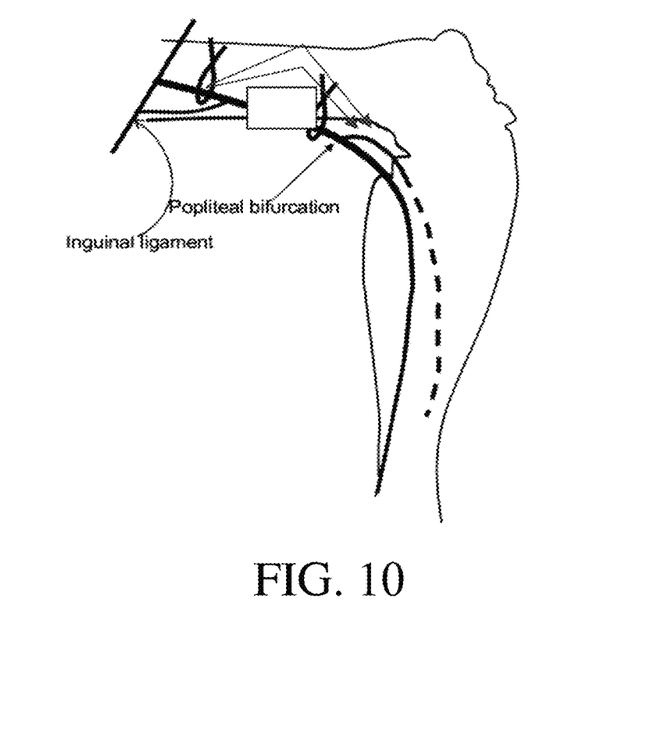
FIG. 10: Mouse Hind Limb: The femoral artery is ligated and portion in between the ligatures is dissected free and excised (shown by the box) so that two ends of the vessel cannot rejoin and the local area is vascularised only by forming more collateral capillaries.

FIG. 10 explains the femoral occlusion surgery and concept of increased collateral vessel formation to circumvent arterial occlusion.

Examples of oligonucleotides that can be used to express p53-specific siRNA in accordance with the invention include but are not limited to
5'GATCCCCGACTCCAGTGGTAATCTACTTCAAGA-GAGTAGATTACCACTGGAGTCTTTTTGGAAA 3' (SEQ ID NO:1) (See Shen et al. FEBS Letters, 539:111-114, 2003, the sequence disclosure of which is incorporated by reference herein);

5'AGCTTTTCCAAAAAGACTCCAGTGGTAATC-TACTCTCTTGAAGTAGATTACCACTGGAGTCGGG 3' (SEQ ID NO: 2) (See Shen et al. FEBS Letters, 539:111-114, 2003, the sequence disclosure of which is incorporated by reference herein).

Other suitable sequences are disclosed by Brummelkamp et al. Science, 296:550-553, 2002, and the disclosure of which is incorporated by reference herein.

The vectors to be used to express p53-specific siRNA in EPC are those that only express their transcripts transiently. Examples include vectors that do not integrate into the chromosomal DNA of the EPC, and thus preferably are not retroviral in nature.

The EPC may be administered with a pharmaceutically acceptable carrier. A pharmaceutically acceptable carrier is a pharmaceutically acceptable material, composition or vehicle, such as a liquid or solid filler, diluent, excipient, solvent or encapsulating material, involved in carrying or transporting a prophylactically or therapeutically active agent, including cells. Each carrier must be "acceptable" in the sense of being compatible with the other ingredients of the formulation and not injurious to the subject. Some examples of materials which can serve as pharmaceutically acceptable carriers include sugars, such as lactose, glucose and sucrose; glycols, such as propylene glycol; polyols, such as glycerin, sorbitol, mannitol and polyethylene glycol; esters, such as ethyl oleate and ethyl laurate; buffering agents, such as magnesium hydroxide and aluminum hydroxide; pyrogen-free water; isotonic saline; Ringer's solution; ethyl alcohol; phosphate buffer solutions; and other non-toxic compatible substances employed in pharmaceutical formulations.

The EPC are administered in effective amounts. An effective amount is that amount of an agent, including a cell or cell population, that stimulates the desired outcome. The absolute amount will depend upon a variety of factors, including the material selected for administration, whether the administration is in single or multiple doses, and individual patient parameters including age, physical condition, size, weight, and the stage of the disease. These factors are well known to those of ordinary skill in the art and can be addressed with no more than routine experimentation. The effective amount may be an amount that ameliorates in whole or in part PVD in a subject, including a diabetic subject.

EPC will typically be administered locally. Such local administration may be subcutaneous, intravenous, intramuscular, and the like, provided the injection site is near the region of the body being treated. As an example, if the lower limb is being treated, the EPC may be administered locally to the vasculature of the affected limb, or to the tissue surrounding the affected vasculature.

REFERENCES

1. NIDDK. National diabetes statistics: 2007 and 2011 fact sheet. Bethesda, Md., USA. Department of Health and Human Services, NIH, 2008 and National Center for Chronic Disease Prevention and Health Promotion, 2011.

2. Kalka C, Isner J, Asahara T et al. (2000) Transplantation of ex vivo expanded endothelial progenitor cells for therapeutic neovascularization. Proc. Natl. Acad. Sci. 97: 3422-3427.

3. Kawamoto A, Losordo D W, Isner J M, Asahara T (2003) Intramyocardial transplantation of autologous endothelial progenitor cells for therapeutic neovascularization of myocardial ischemia. Circulation 107: 461-468.

4. Asahara T, Murohara T, Isner J M et al. (1997) Isolation of putative progenitor endothelial cells for angiogenesis. Science 275: 964-967.

5. Sen S, Merchan J, Dean J, Ii M, Gavin M, Silver M, Tkebuchava T, Yoon Y S, Rasko J E, Aikawa R. (2010) Autologous transplantation of endothelial progenitor cells genetically modified by adeno-associated viral vector delivering IGF-1 gene following myocardial infarction. Human Gene Therapy 21: 1327-1334

6. Losordo D W, Henry T D, Davidson C, Sup Lee J, Costa M A, Bass T, Mendelsohn F, Fortuin F D, Pepine C J, Traverse J H, Amrani D, Ewenstein B M, Riedel N, Story K, Barker K, Povsic T J, Harrington R A, Schatz R A; Intramyocardial, Autologous CD34+Cell Therapy for Refractory Angina: ACT34-CMI Investigators. Circ Res. 2011 Aug. 5;109(4):428-36. Epub 2011 Jul. 7.

7. Losordo D W, Schatz R A, White C J, Udelson J E, Veereshwarayya V, Durgin M, Poh K K, Weinstein R, Kearney M, Chaudhry M, Burg A, Eaton L, Heyd L, Thorne T, Shturman L, Hoffmeister P, Story K, Zak V, Dowling D, Traverse J H, Olson R E, Flanagan J, Sodano D, Murayama T, Kawamoto A, Kusano K F, Wollins J, Welt F, Shah P, Soukas P, Asahara T, Henry T D. Intramyocardial transplantation of autologous CD34+ stem cells for intractable angina: a phase I/IIa double-blind, randomized controlled trial. Circulation. 2007 Jun. 26;115(25):3165-72. Epub 2007 Jun. 11.

8. Sen S, Conroy S, Hynes S O, McMahon J, O'Doherty A, Bartlett J S, Akhtar Y, Adegbola T, Connolly C E, Sultan S, Barry F, Katusic Z S, O'Brien T. (2008) Gene delivery to the vasculature mediated by low-titre adeno-associated virus serotypes 1 and 5. J Gene Med. 2008 February;10(2):143-51.

9. Mund J A, Ingram D A, Yoder M C, Case J (2009) Endothelial stem cells and cardiovascular cell-based therapies. Cytotherapy 11: 103-113.

10. Standards of Medical Care in Diabetes-2011, Diabetes Care, January 2011 vol. 34 no. Supplement 1 S11-S61.

11. Rosso A, Balsamo A, Brizzi M F et al. (2006) p53 Mediates the accelerated onset of senescence of endothelial progenitor cells in diabetes. J Biol Chem 281: 4339-4347

12. Utikal J, Polo J M, Stadfeld M et al. (2009) Immortalization eliminates a roadblock during cellular reprogramming into iPS cells. Nature 460: 1145-1148

13. Kappel S, Matthess Y, Strebhardt K (2007) Silencing of mammalian genes by tetracycline-inducible shRNA expression. Nature Protocols 2: 3257-3269

14. Nishiyama T, Mishima K, Ide F et al. (2007) Functional Analysis of an Established Mouse Vascular Endothelial Cell Line. J. Vasc. Res. 44: 138-148

15. Ventura A, Meissner A, Dillon C P et al. (2004) Cre-lox-regulated conditional RNA interference from transgenes. Proc. Natl. Acad. Sci. 101: 10380-10385

16. Morales D E, McGowan K A, Grant D S et al. (1995) Estrogen promotes angiogenic activity in human umbilical vein endothelial cells in vitro and in a murine model. Circulation 91: 755-763

17. Compton S, Kim C, Griner N B, Potluri P, Scheffler I E, Sen S, Jerry D J, Schneider S, Yadava N. Mitochondrial Dysfunction Impairs Tumor Suppressor p53 Expression/Function. J Biol Chem. 2011 Jun. 10;286 (23):20297-312.

EQUIVALENTS

This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

What is claimed is:

1. A method comprising
locally administering to a subject having type 1 diabetes an endothelial progenitor cell genetically modified to have transiently reduced p53 expression for about 2-4 weeks in an effective amount to treat vascular conditions associated with type 1 diabetes.

2. The method of claim 1, wherein the endothelial progenitor cell is a CD34+ cell.

3. The method of claim 2, wherein the CD34+ cell is obtained from blood.

4. The method of claim 1, wherein the endothelial progenitor cell is obtained from the subject being treated.

5. The method of claim 1, wherein the endothelial progenitor cell is obtained from a donor that is not the subject being treated.

6. The method of claim 1, wherein the endothelial progenitor cell expresses p53-specific siRNA.

7. The method of claim 6, wherein the p53-specific siRNA is expressed from a non-integrating vector.

8. The method of claim 6, wherein the p53-specific siRNA is expressed from an adenovirus.

9. The method of claim 1, wherein the endothelial progenitor cell is administered to the subject more than once.

10. The method of claim 9, wherein the endothelial progenitor cell is administered to the subject once a month, once every two months, once every three months, or once every six months.

11. The method of claim 1, wherein the endothelial progenitor cell is administered to a limb of the subject.

12. The method of claim 11, wherein the endothelial progenitor cell is administered to a lower limb of the subject.

13. The method of claim 1, wherein the subject has impaired wound repair.

14. The method of claim 1, wherein the subject has peripheral vascular disease.

15. The method of claim 1, wherein p53 expression is transiently reduced during differentiation of the endothelial progenitor cell to a mature endothelial cell.

16. A method comprising
locally administering to a subject having type 1 diabetes an endothelial progenitor cell genetically modified to have transiently reduced p53 expression in an effective amount to enhance collateral circulation in the subject, wherein p53 expression is transiently reduced during differentiation of the endothelial progenitor cell to a mature endothelial cell.

* * * * *

SEQUENCE LISTING

```
<160> NUMBER OF SEQ ID NOS: 2

<210> SEQ ID NO 1
<211> LENGTH: 64
<212> TYPE: DNA
<213> ORGANISM: Artificial Sequence
<220> FEATURE:
<223> OTHER INFORMATION: Synthetic Polynucleotide

<400> SEQUENCE: 1
gatccccgac tccagtggta atctacttca agagagtaga ttaccactgg agtcttttg    60 gaaa                                                                 64

<210> SEQ ID NO 2
<211> LENGTH: 64
<212> TYPE: DNA
<213> ORGANISM: Artificial Sequence
<220> FEATURE:
<223> OTHER INFORMATION: Synthetic Polynucleotide
```

-continued

```
<400> SEQUENCE: 2
agcttttcca aaaagactcc agtggtaatc tactctcttg aagtagatta ccactggagt    60
cggg                                                                64
```